United States Patent [19]
Tsujino et al.

[11] 4,009,079
[45] Feb. 22, 1977

[54] METHOD FOR QUANTITATIVELY DETERMINING GLUCOAMYLASE IN HUMAN URINE AND BODY FLUIDS

[75] Inventors: Kazuaki Tsujino; Junnosuke Kida, both of Osaka; Masanobu Hosotani, Takatsuki; Noshi Minamiura, Nara; Takehiko Yamamoto, Izumi, all of Japan

[73] Assignee: Ono Pharmaceutical Co., Ltd., Osaka, Japan

[22] Filed: Jan. 26, 1976

[21] Appl. No.: 652,012

[30] Foreign Application Priority Data

Jan. 24, 1975  Japan .............................. 50-10731

[52] U.S. Cl. .................. 195/103.5 R; 195/103.5 C
[51] Int. Cl.² ........................................ G01H 31/14
[58] Field of Search .............. 195/103.5 R, 103.5 C

[56] References Cited
OTHER PUBLICATIONS

Chem. Abstracts, vol. 79, 1973, 50268v, p. 114, "Kinetic Studies of Glucoamylase".

*Primary Examiner*—A. Louis Monacell
*Assistant Examiner*—C. A. Fan
*Attorney, Agent, or Firm*—Sughrue, Rothwell, Mion, Zinn & Macpeak

[57] ABSTRACT

A method for quantitatively determining glucoamylase in human urine and body fluids which comprises removing low molecular weight substances from a human urine or body fluid sample, adding to the resulting sample which is free of low molecular weight (from about 500 to about 20,000) substances maltotriitol, phenyl-α-glucoside or 2,4-dinitrophenyl-α-glucoside, which are specific substrates for glucoamylase, and quantitatively determining the glucose, phenol or 2,4-dinitrophenol which is a degradation product of the above substrates, respectively.

1 Claim, 4 Drawing Figures

METHOD FOR QUANTITATIVELY DETERMINING GLUCOAMYLASE IN HUMAN URINE AND BODY FLUIDS

BACKGROUND OF THE INVENTION

1. Field of the Invention

This invention relates to a method of clinical diagnosis, more particularly, to a method for quantitatively determining the enzymatic activity of glucoamylase present in urine or body fluids using maltotriitol, phenyl-α-glucoside or 2,4-dinitrophenyl-α-glucoside, based on the substrate specificity of glucoamylase without being influenced by the presence of other amylases.

2. Description of the Prior Art

It was found by one of the present inventors that glucoamylase is usually present in urine (Minamiura, N. et al., J. Biochem. 72, 1295 (1972)).

It is also known that glucoamylase originates in the liver, and a relationship between glucoamylase and disorders of the liver and the other organs has been noted.

Therefore, it has been desired to develop a method for quantitatively determining the enzymatic activity of traces of glucoamylase contained in human urine or body fluids.

Generally, in determining amylase activity a buffer solution is added to an enzyme solution to maintain optimum pH, and a substrate is added thereto to allow the mixture to react at an appropriate temperature. After a prescribed period of time, the amount of reduced sugar degradation product is chemically or enzymatically determined to calculate the enzymatic activity.

It is rare that only one type of amylase is produced in an organism. The amylase always exist as a mixture of several kinds. Further, any of the substrates for which each of the amylases is specific is degraded by the amylases to glucose or polymers or oligomers of glucose, e.g., maltose, isomaltose, cyclic dextrin or the like, and, therefore, it is impossible to correlate the degradation products with one kind of amylase, thereby making it difficult to determine the amount of a specific amylase. In practice, quantitative analysis has been carried out by taking into consideration other properties of the amylases.

Several determination methods are conventionally employed which can be selected depending upon the enzyme source and the enzyme whose determination is desired. These can be classified as follows:

1. Thermally resistant amylases and acid resistant amylases are separated.
2. Saccharogenic amylases and liquefying amylases are separated.
3. The degree of polymerization of the degradation product is determined by an iodine method.
4. A specific dextrin is used as a substrate.

With any of these conventional methods, it is difficult to obtain an exact fractional determination.

Glucoamylase is classified as a saccharogenic amylase which produces only glucose from starch glycogen; a fractional determination method therefor distinguishing it from other amylases present which are also capable of producing glucose has not yet been reported.

SUMMARY OF THE INVENTION

One object of this invention is to provide a method for quantitatively determining glucoamylase present in urine or body fluids.

DETAILED DESCRIPTION OF THE INVENTION

Figure 1:
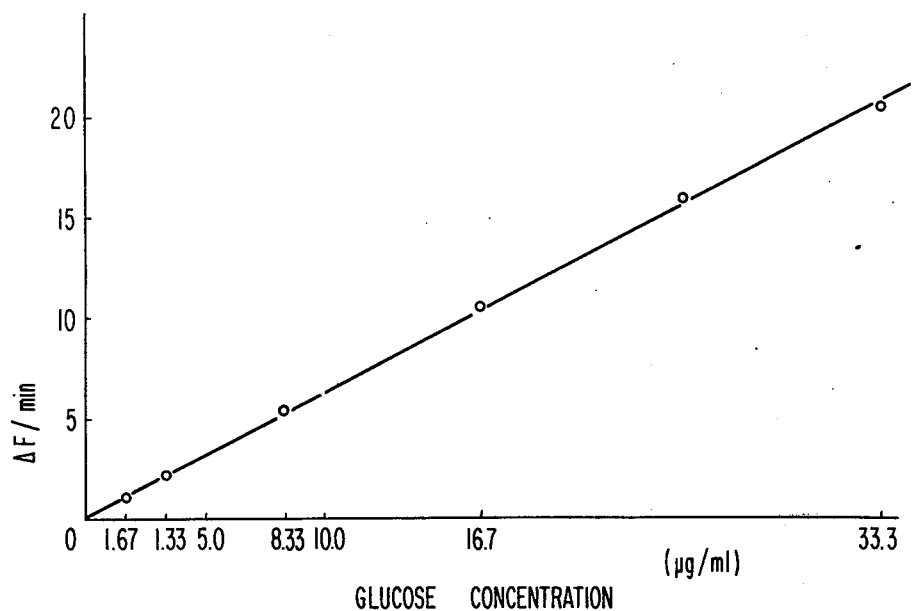
FIG. 1 is a standard curve for determining glucose concentrations according to a fluorescence method.

The term "body fluids" used throughout the specification and claims mean blood, lymph, excreta except urine, and the like.

Various investigations have been conducted by the inventors on the complicated substrate specificity of the amylases using oligosaccharides. Following the routine set out below, the inventors discovered several facts.

An acetic acid buffer solution at a pH of 5.0 was added to crystalline α-amylase (Bacillus subtilis), crystaline β-amylase (malt) or crystalline glucoamylase (Rhizopus sp.), all of which are commercially available. Each of the oligosaccharides as indicated in Table 1 was added thereto as a substrate, and the resulting mixture reacted at a temperature of 37° C for 2 hours. The amount of glucose produced in each reaction mixture was determined by the Park Johnson method (Sakuzo Fukui: A Method for Determining Reduced Sugar, p. 15, published by Tokyo University Publication Department) to analyze the amylase activity for each substrate. As a result, the substrate specificity of α-amylase, β-amylase or glucoamylase was as shown in Table 1, which establishes that α-amylase, β-amylase and glucoamylase cannot be distinguished with respect to their individual activity for substrates consisting of glucose alone.

However, it was also found that maltotriitol, phenyl-α-glucoside and 2,4-dinitrophenyl-α-glucoside each having a compound other than glucose bonded to a part of the structure of the substrate are exclusively degraded by glucoamylase, but are not degraded by α-amylase or β-amylase.

TABLE 1

| Oligo-saccharide | α-Amylase | β-Amylase | Glucoamylase Rhizopus sp. | Glucoamylase Urine | Degradation Product |
|---|---|---|---|---|---|
| maltose | − | − | + | + | glucose |
| maltotriose | + | + | + | + | glucose |
| maltotriitol | − | − | + | + | glucose maltitol |
| maltotetraose | + | + | + | + | glucose |
| phenyl-α-glucoside | − | − | + | + | glucose phenol |

TABLE 1-continued

| Oligo-saccharide | α-Amylase | β-Amylase | Glucoamylase Rhizopus sp. | Glucoamylase Urine | Degradation Product |
|---|---|---|---|---|---|
| 2,4-dinitro-phenyl-α-glucoside | − | − | + | + | glucose 2,4-dinitrophenol |

Note:
The mark "+" indicates that the test oligosaccharide was degraded.
The mark "−" indicates that the test oligosaccharide was not degraded.

The amounts of degradation products, i.e., glucose, phenol and 2,4-dinitrophenol, can be determined by the known methods. Therefore, the amount of glucoamylase present in an amylase mixture can be quantitatively measured, taking advantage of its specificity for maltotriitol, phenyl-α-glucoside and 2,4-dinitrophenyl-α-glucoside.

The reaction conditions for glucoamylas in the case where the substrate is maltotriitol are as follows:

1. 0.3 ml of a 1M acetic acid buffer solution at a pH of from about 4.0 to about 6.0 is added to 3.0 ml of a urine or body fluid sample (with final concentration of acetic acid in the sample being ca. 0.091M) from which low molecular weight substances had been removed by dialysis or gel filtration (substances having a molecular weight of from about 500 to about 20,000);
2. 0.3 ml of a maltotriitol solution at a concentration of from about 0.1 to about 10 μg/ml is added to the resulting mixture;
3. the mixture is maintained at a temperature of from about 28° to about 55° C for a period of from about 10 to about 60 minutes; and
4. 0.25 ml of a 1M tris(hydroxymethyl)aminomethane solution (hereinafter referred to as a "tris buffer solution") is added to the reaction mixture to stop reaction. In order to stop reaction it is sufficient to render the reaction system to a pH higher than 8 to 8.5, and the above-defined amount of a 1M tris solution is satisfactory for this purpose.

The glucoamylase activity can be calculated according to the following equation:

$$\text{Glucoamylase Activity (units)} = \frac{\text{Amount of Glucose Produced in 10 Minutes of Reaction (}\mu\text{ mole)}}{10}$$

The term "unit" defines the activity of an enzyme determined in terms of the amount (μ moles) of substrate degraded per the time (minutes) required to enzymatically degrade such an amount of substrate, i.e., the activity capable of degrading 1 μ mole of substrate in 1 minute.

The reaction conditions employed in the case where phenyl-α-glucoside or 2,4-dinitrophenyl-α-glucoside is used as a substrate will hereinafter be presented.

Determination of degradation products can be carried out as follows:

1. Determination of glucose by an enzyme method can be carried out according to the method by Guilbault et al., described in Anal. Chem. 40, 190 (1968). That is, a tris buffer solution at a pH of 8.5 is added to an aqueous glucose solution, and to a 2.7 ml aliquot thereof are added 0.1 ml of a glucose oxidase (obtained from Aspergillus niger Type II (Sigma Chemical Co.)) solution having a concentration of 2 mg/ml, 0.1 ml of a peroxidase (obtained from Horse radish Type I (Sigma Chemical Co.)) solution having a concentration of 1 mg/ml and 0.1 ml of a homovanillic acid solution having a concentration of 2.5 mg/ml. The increase in fluorescence with the passage of time (Δ F/min) is then determined using a spectrophotofluorometer at an excitation wavelength of 330 nm and a fluorescence wavelength of 430 nm. The standard curve representing the relationship between the thus obtained glucose concentrations in the sample and the Δ F/min values is shown in FIG. 1.

The amount of glucose contained in the degradation mixture obtained by the activity of glucoamylase present in urine or body fluids can be determined utilizing the standard curve as given in FIG. 1. It should be noted, however, that in case of a urine sample which generally contains acidic substances such as uric acid, 0.25 ml of a 1M tris solution instead of the tris buffer solution at a pH of 8.5 is added to 3.6 ml of the reaction mixture to provide a reaction system pH of 8.5.

Figure 2:
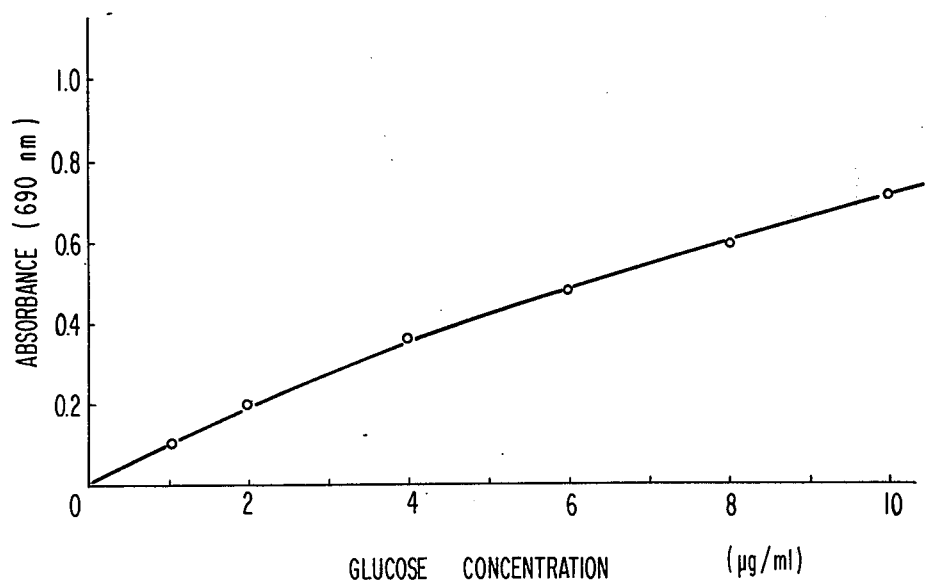
FIG. 2 is a standard curve for determining glucose concentrations according to the Park Johnson method.

2. Quantitative determination of reduced sugar was performed in accordance with the aforesaid Park Jonson method except that the addition of potassium cyanide as a stabilizer is omitted. That is, a mixture of 3 ml of a glucose solution, 1 ml of an aqueous solution of potassium ferricyanide at a concentration of 0.5 g/l and 1 ml of sodium carbonate solution at a concentration of 5.3 g/l was maintained in boiling water for 15 minutes followed by cooling to room temperature with flowing water. 5 ml of a 0.05N sulfuric acid solution comprising 1.5 g/l of iron alum and 1 g/l of sodium dodecylsulfate was added to the mixture and the system then allowed to stand at room temperature for 15 minutes followed by colorimetric analysis using a spectrophotometer at a wavelength of 690 nm. The standard curve representing the relationship beetweem the thus obtained glucose concentrations of the samples and the absorbance thereof is shown in FIG. 2.

3. Quantitative determination of phenol obtained from phenyl-α-glucoside can be carried out as follows. 2 ml of a 0.005M acetic acid buffer solution at a pH of 5.0 containing phenyl-α-glucoside at a concentration of 1.5 μ mol/ml, i.e., 410 μg/ml, was mixed with 1 ml of urine or a body fluid having low molecular weight materials removed therefrom by dialysis or gel filtration (final concentration of acetic acid in the sample is ca. 0.0033M) and allowed to stand at a temperature of from about 28° to 55° C for a period of time in which optical density at a wavelength of 270 nm was proportional to the passage of time and the increase in absorbance at a wavelength of 270 nm was determined using a spectrophotometer at a definite time or with the passage of time. The glucoamylas activity unit can be obtained from the increase in absorbance per minute (Δ OD/min) according to the following equation:

$$\text{Glucoamylase Activity (Unit)} = \frac{\Delta \text{OD/min} \times 3}{\text{phenol}/\mu \text{ MOD (1.450)}}$$

Determination of 2,4-dinitrophenol produced from 2,4-dinitrophenyl-α-glucoside:

In the same manner as described in (3) above, the increase in absorbance at a wavelength of 362 nm was determined using a spectrophotometer but using as the substrate, 2,4-dinitrophenyl-α-glucoside in place of phenyl-α-glucoside. The glucoamylase activity unit can be obtained according to the following equation:

$$\text{Glucoamylase Activity (Unit)} = \frac{\Delta \text{OD/min} \times 3}{\text{2,4-Dinitrophenol}/\mu \text{ MOD (12.2)}}$$

In the following, a process for removing low molecular weight substances from samples will be described.

The removal of low molecular weight substances from urine or serum can be carried out by dialysis or gel filtration.

The dialysis can be conducted by using an acetic acid buffer solution at a pH of 4.5 with a change every 3 to 4 hours at about 4° C for a period of from about 1 to 2 days.

Figure 3:
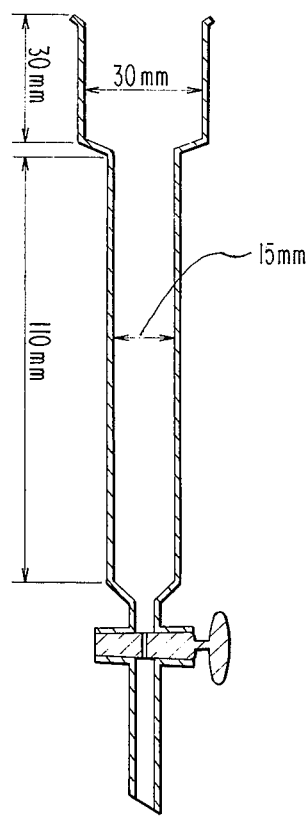
FIG. 3 is a schematic view of a column used in the present invention for gel-filtration.

Gel filtration can be carried out by charging a column as schematically illustrated in FIG. 3 with 1 g (dry weight) of Biogel P-10 (trade name for a molecular sieve made from polyacrylamide having an average molecular weight of about 1,000,000 or more manufactured by Bio-Rad Laboratory) which has previously been swollen in deionized water, and two 3 ml portions of urine or serum are passed therethrough from the top of the column to obtain 2 fractions. The second fraction is used as a treated urine or treated serum with the first fraction being discarded.

Of course, any other molecular sieve can also be employed which has a molecular sieve effect enabling one to obtain by fractionation desired substances having a molecular weight of from about 4,000 to about 40,000. For example, Sephadex G-100 (trade name for a molecular sieve made from dextran having an average molecular weight of about 1,000,000 or more manufactured by Pharmacia Fine Chemicals) can be used.

Figure 4A:
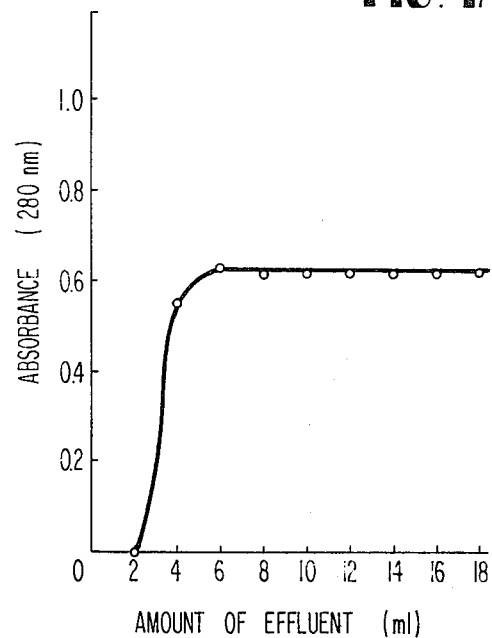
FIG. 4 shows examples of urine fractions obtained by column chromatography using Biogel P-10 (a trade name of a molecular sieve manufactured by Bio-Rad Laboratory) where FIG. 4 (a) represents the behavior of bovine serum albumin added to urine and FIG. 4 (b) represents the behavior of ultraviolet absorbant substances, glucose and fluorescent substances.
Figure 4B:
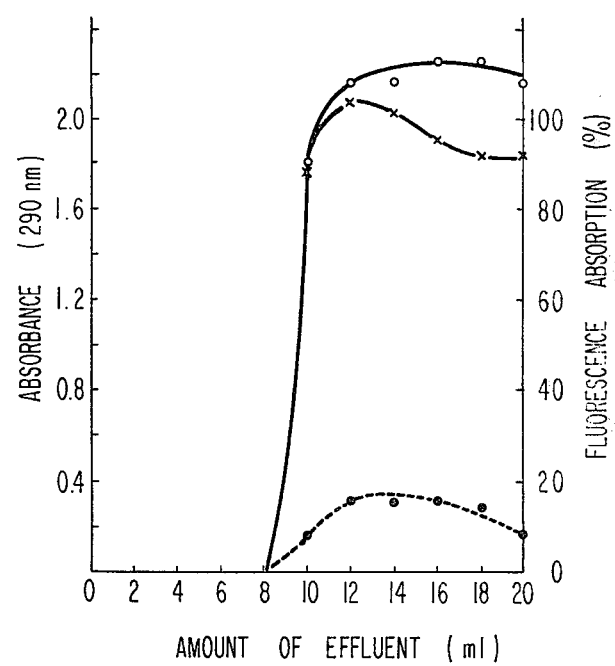

The behavior which low molecular weight substances and high molecular weight substances exhibited during the above described column treatment are plotted in FIG. 4. The 1% bovine serum albumin added as a sample appeared in the second fraction (cf. FIG. 4 (a)). It was in further succeeding fractions that the reduced sugars, fluorescent substances, ultraviolet absorbants and the like inherently contained in urine or blood were eluted (cf. FIG. 4 (b)).

Comparative studies were conducted between dialyzed urine and the column treated urine for glucoamylase activity. Urine samples were divided into two portions. One portion was dialyzed and the other column treated (both as described above), and the glucoamylase activity of each portion was determined using the aforesaid fluorescence method of Guilbault et al. The results obtained are shown in Table 2.

TABLE 2

| Sample No. | Dialyzed Urine (munit)* | Column Treated Urine (munit) |
|---|---|---|
| 1 | 1.6 | 1.8 |
| 2 | 0.9 | 1.0 |
| 3 | 1.2 | 1.2 |
| 4 | 0.7 | 0.6 |
| 5 | 0.7 | 0.5 |
| 6 | 1.4 | 1.6 |

*munit = 1/1,000 of a unit

There was observed no significant difference in the data obtained depending upon the type of low molecular weight substance removed used, as judged by the results given above wherein two portions from one sample both showed substantially equal activities.

The invention will now be illustrated in greater detail with reference to Examples, which are not, however, to be construed as limiting the invention. Unless otherwise indicated, all processings were at atmospheric pressure and room temperature.

EXAMPLE 1

10 ml of human urine was dialyzed agaist a 0.02M acetic acid buffer solution at a temperature of 5° to 10° C at a pH of 4.5 for 48 hours. 3.0 ml of the thus obtained dialyzed urine, 0.3 ml of a maltotriitol solution at a concentration of 1 mg/ml and 0.3 ml of a 1M acetic acid buffer solution at a pH of 5.5 were mixed and the mixture allowed to react at 40° C for 10 minutes. Immediately thereafter, 0.25 ml of a 1M tris solution was added to the reaction mixture to adjust the pH to 8.5, thereby stopping the reaction. A 2.7 ml aliquot of the resulting mixture was placed in a fluorescence photometer cell, and 0.1 ml of a homovanillic acid solution at a concentration of 2.5 mg/ml, 0.1 ml of a peroxidase (obtained from Aspergillus niger Type II (Sigma Chemical Co.)) solution at a concentration of 1 mg/ml and 0.1 ml of a glucose oxidase (obtained from Horse radish Type I (Sigma Chemical Co.)) solution at a concentration of 2 mg/ml were added thereto. The increase in fluorescence (Δ F/min) was 1.5, which value was applied to the standard curve of FIG. 1 to find that the glucose concentration in the reaction mixture was 233 μg/ml. Since the volume of the reaction mixture was 3.85 ml based on the sum of the urine, the maltotriitol solution, the acetic acid buffer solution and the tris solution, the amount of the glucose produced turned out to be 2.33 × 3.85 = 8,97 μg. According to the definition that "glucoamylase activity is the μ molar amount of glucose produced in 1 minute of reaction," the glucoamylase activity in the test urine sample was calculated by the following equation:

$$\text{Glucoamylase Activity (Unit)} = \frac{\text{Amount of Glucose Produced}}{\text{Molecular Weight of Glucose}} \times \frac{1}{\text{Amount of Urine (ml)}}$$

$$\times \frac{1}{\text{Reaction Time (min)}} = \frac{8.97}{180} \times \frac{1}{3} \times \frac{1}{10} = 0.0017 \text{ unit/ml}$$

Defining 1/1,000 of 1.0 unit as a munit, the above obtained result were expressed as 1.7 munit.

EXAMPLE 2

6 ml of human urine was passed through a column packed with 1 g of Biogel P-10 which had previously been swollen in deionized water, with the first 3 ml of the effluent being discarded. To the last 3 ml of effluent were added 0.3 ml of a maltotriitol solution at a concentration of 1 mg/ml and 0.3 ml of a 1M acetic acid buffer solution at a pH of 5.5, followed by allowing the mixture to react at 40° C for 10 minutes. Upon completion of the reaction, 0.25 ml of a 1M tris solution was added to the reaction mixture to stop the reaction. A 2.7 ml aliquot of the resulting reaction mixture was taken out and worked up in the same manner as described in Example 1 to find $\Delta$ F/min to be 2.0. This value was applied to the standard curve of FIG. 1 to obtain a 2.96 $\mu$/ml glucose concentration in the reaction mixture. Accordingly, the amount of the glucose produced in the total reaction mixture was calculated as 2.96 × 3.85 = 11.4 $\mu$g. From this value the glucoamylase activity was calculated in the same manner as described in Example 1 as follows:

glucoamylase activity in urine was calculated as follows:

$$\text{Glucoamylase Activity} = \frac{\text{Glucose Concentration}}{\text{Glucose Molecular Weight}} \times \frac{\text{Amount of Reaction Mixture}}{\text{Amount of Urine Used}}$$

$$\times \frac{1}{10} = \frac{4.2}{180} \times \frac{3.85}{3} \times \frac{1}{10} = 0.0030 \text{ unit/ml}$$

$$= 3.0 \text{ munit/ml}$$

EXAMPLE 4

6 ml of human urine was passed through a column packed with 1 g of Biogel P-10 which had previously been swollen in deionized water, with the first 3 ml of the effluent being discarded. The last 3 ml of effluent was divided into two 1.5 ml portions, which were designated as A and B, respectively. 0.15 ml of a maltotriitol solution at a concentration of 1 mg/ml and 0.15 ml of a 1M acetic acid buffer solution at a pH of 5.5 were added to A while 0.15 ml of dionized water and 0.15 ml of a 1M acetic acid buffer solution at a pH of 5.5 were added to B. After each of portions A and B was reacted at 40° C for 10 minutes, 0.125 ml of a 1M tris solution as added thereto to adjust the pH to 8.5, thereby stopping the reaction. The resulting reaction mixture was $$\text{Glucoamylase Activity} = \frac{11.4}{180} \times \frac{1}{3} \times \frac{1}{10} = 0.0021 \text{ unit/ml} = 2.1 \text{ munit/ml}$$

EXAMPLE 3

In the same manner as described in Example 1, two 3 ml portions of a dialyzed urine sample were prepared and designated as A and B, respectively. 0.3 ml of a maltotriitol solution at a concentration of 1 mg/ml and 0.3 ml of a 1M acetic acid buffer solution at a pH of 5.5 were added to A, whereas to B 0.3 ml of deionized water and 0.3 ml of a 1M acetic acid buffer solution at a pH of 5.5 were added followed by allowing each of the resulting mixtures to react at 40° C for 10 minutes, whereafter 0.25 ml of a 1M tris solution was added to adjust the pH to 8.5, thereby stopping the reaction. Each reaction mixture was diluted 3 fold times with deionized water, and 3 ml aliquots removed from each sample were designated test sample A and B, respectively. To each of test samples A and B were added 1 ml of a potassium ferricyanide solution (concentration of 0.5 g/l) and 1 ml of a sodium carbonate solution (concentration of 5.3 g/l), and the resulting mixture was placed in boiling water for 15 minutes followed by cooling with flowing water to room temperature. 5 ml of a 0.05N sulfuric acid solution comprising 1.5 g/l of iron alum and 1 g/l of sodium dodecyl sulfate were then added to the mixture followed by allowing the mixture to stand for 15 minutes to complete formation. The colorimetric determination of the blue color thus formed at a wavelength of 690 nm revealed that the absorbance of A and B was 0.244 and 0.120, respectively. Subtracting B from A, the result was 0.124, which indicated the degree of color formation due to the glucose in the reaction mixture. Applying the above value to the standard curve of FIG. 2, the glucose concentration was found to be 1.4 $\mu$g/ml. As the reaction mixture had been diluted 3 fold times, 1.4 was multiplied by 3 making 4.2 $\mu$g/ml, which corresponded to the glucose concentration in the reaction mixture. The diluted 3 fold times with deionized water. The amount of the glucose in a 3 ml aliquot of each mixture was obtained in the same manner as described in Example 3. The absorbance of A and B was 0.220 and 0.135, respectively, whereby A minus B equals 0.085, which indicated the color formation due to glucose in the reaction mixture. This value was then applied to the standard curve of FIG. 1 to find the glucose concentration was 0.9 $\mu$g/ml, which was multiplied by 3 (making 2.7 $\mu$g/ml the glucose concentration in the reaction mixture). Following the same equation as described in Example 3, the glucoamylase activity in urine was obtained as follows:

$$\frac{2.7}{180} \times \frac{3.85}{3} \times \frac{1}{10} = 0.0019 \text{ unit/ml} = 1.9 \text{ munit/ml.}$$

EXAMPLE 5

10 ml of human urine was dialyzed against a 0.02M acetic acid buffer solution at a temperature of 5° to 10° C at a pH of 4.5 for 48 hours. To 1.0 ml of the thus obtained dialyzed urine, 2 ml of a 0.005M acetic acid buffer solution at a pH of 5.0 containing 1.5 $\mu$M/ml of phenyl-$\alpha$-glucoside was added followed by mixing at a temperature of 40° C for 5 minutes. The increase in absorbance $\Delta$ OD/min at a wavelength of 270 nm was found to be 0.0013 as determined with the passage of time, and, accordingly, the glucoamylase activity was calculated from the molar absorbancy index of phenol (1,450) to be 1.71 munit.

EXAMPLE 6

In the same manner as described in Example 5 but using 2,4-dinitrophenyl-$\alpha$-glucoside in place of phenyl-$\alpha$-glucoside, the increase in absorbance $\Delta$ OD/min at a wavelength of 362 nm was determined to be 0.0065.

The glucoamylase activity was calculated from the molar absorbancy index of 2,4-dinitrophenol (12,200) to be 1.59 munit.

While the invention has been described in detail and with reference to specific embodiments thereof, it will be apparent to one skilled in the art that various changes and modifications can be made therein without departing from the spirit and scope thereof.

What is claimed is:

1. A method for determining the amount of glucoamylase in human urine and body fluids which comprises removing low molecular weight substances having a molecular weight of from about 500 to about 20,000 from a human urine or body fluid sample, adding to the resulting sample which is free of low molecular weight substances maltotriitol which is a specific substrate of glucoamylase, and measuring the amount of glucose, which is the degradation product of the substrate.

* * * * *